United States Patent
Jaffe

(10) Patent No.: US 7,160,108 B2
(45) Date of Patent: Jan. 9, 2007

(54) ALL-IN-ONE PROPHY ANGLE

(76) Inventor: Carlos Daniel Jaffe, 305 Orange Ave. Suite C, Huntington Beach, CA (US) 92648

( * ) Notice: Subject to any disclaimer, the term of this patent is extended or adjusted under 35 U.S.C. 154(b) by 287 days.

(21) Appl. No.: 10/632,505

(22) Filed: Aug. 4, 2003

(65) Prior Publication Data
US 2005/0032022 A1 Feb. 10, 2005

(51) Int. Cl.
A61C 3/06 (2006.01)
A61C 5/04 (2006.01)

(52) U.S. Cl. .......................... 433/125; 433/89; 433/84

(58) Field of Classification Search ............... 433/82, 433/87, 83, 84, 85, 80, 89, 41
See application file for complete search history.

(56) References Cited

U.S. PATENT DOCUMENTS 5,642,994 A * 7/1997 Chipian et al. ............... 433/82

* cited by examiner

Primary Examiner—Cary E. O'Connor
Assistant Examiner—Candice C. Stokes
(74) Attorney, Agent, or Firm—Neil John Graham

(57) ABSTRACT

The all-in-one prophy angle for cleaning teeth contains a self dispensing solid core prophy polish which allows the operator to perform an entire prophylaxis of the teeth with the efficiency of not having to remove the handpiece from the mouth, further, cross contamination from splatter is minimal to none. The prophy cup and solid core polish are in a changeable cartridge form allowing the prophy handpiece to be reusable.

25 Claims, 3 Drawing Sheets

ALL-IN-ONE PROPHY ANGLE

BACKGROUND OF THE INVENTION

This invention relates to dental prophylactic (prophy) angle handpieces, prophy cups, and prophy polish for professional cleaning of teeth.

Rotating prophy cups are generally used to carry and apply prophy paste to the teeth. The prophy paste is comprised of an abrasive, a binder, and a liquefying agent which is used to create a flow of the paste. The prophy cup functions by carrying the prophy paste to the surface of the teeth and the cup material polishes all surfaces of the teeth, including subgingival and interproximal surfaces. Typically the prophy cup picks up the paste by dipping the cup in a reservoir of paste. As the cup is rotated by the prophy angle, the prophy paste exits the cavity and is applied to the tooth. The paste acts as both a lubricant and an abrasive.

Due to the centrifugal rotation of the prophy cup the pumice quickly exit exits the cup and splatters throughout the mouth and on the patient and operator, increasing the risk of cross contamination. Prophy cups have been designed in an attempt to slow down the exiting of the prophy paste. The prophy cup must be repeatedly reloaded, which is time-consuming. Prophy handpieces have been designed to deliver continuous supply prophy paste thus eliminating the need to refill the prophy cup, but do not allow the operator to quickly vary the flow of paste as needed and does not eliminate the splatter problem. A prophy handpiece named the Twist™ U.S. Pat. No. 6,409,507 has been designed to reciprocate 90 degrees rather than to rotate. The Twist™ claims to produce faster prophys, and no tearing or cutting of soft tissue and no frictional heat. The Twist™ represents a reasonable attempt to control splatter, but the reciprocating motion is not as efficient as the rotary motion at polishing teeth and does not deliver a continuous supply of prophy paste.

SUMMARY OF THE INVENTION

The present intervention is directed towards a solid core prophy polish to be used in cleaning teeth. Also included are a dental prophy angle and a prophy cup. The prophy cup is comprised of a longitudinal cylindrical body with an interior and exterior, a rear and front end, the rear end contains a shaft which connects to the prophy angle. The prophy cup front end has a circular polishing edge. Adjacent to the polishing edge, towards the body interior, is a circular retaining edge. Contained within the interior of the body of the prophy cup is the longitudinal solid core prophy polish with circumferential circular rings, which are at right angles to the prophy polish's long axis. The solid core prophy polish has a front end which engages the tooth and a second end with an end plate which engages a disc or piston which is fitted to the interior of the body of the prophy cup and is positioned vertical its long axis. Positioned between the body second end and the piston is a longitudinal spring which supplies a continuous dispensing pressure against the solid core polish. The solid core prophy polish is retained within the interior of the prophy cup by the circular retaining edge which engages the an annular groove of the solid prophy polish. At rest the dispensing force of the spring is countered by the holding force of the retaining edge and the solid core prophy polish is held in place. As the prophy cup is pressed against the tooth surface the annular retaining edge increases in circumference, which releases the retaining edge from the prophy polish's circular ring, which allows the spring to push the polish against the tooth surface, which dispenses the polish during the prophylaxis of the patients teeth. The patient is asked to rinse prior to the prophy which supplies moisture to the tooth surface and rotation of the prophy cup dispenses the prophy polish. The harder the prophy cup is pushed against the tooth surface the quicker the polish is dispatched. The pressure of the tooth against the solid polish counteracts the force of the spring and retains the polish within the prophy cup. Pressure against the tooth dispenses a consistent amount of polish on the tooth. There is no splatter of the prophy polish and the prophy angle may be kept in the mouth from start to finish continuously. The result is minimal, if any, splatter, which reduces cross-contamination and results in a reduction of operating time.

DETAILED DESCRIPTION OF THE INVENTION

Figure 1:
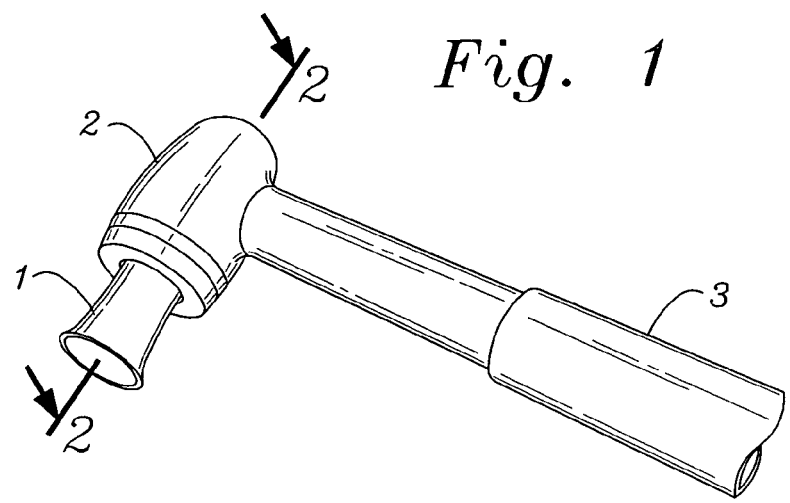
FIG. 1 is a side view of the prophy cup and angle mounted to a dental handpiece.
Figure 2:
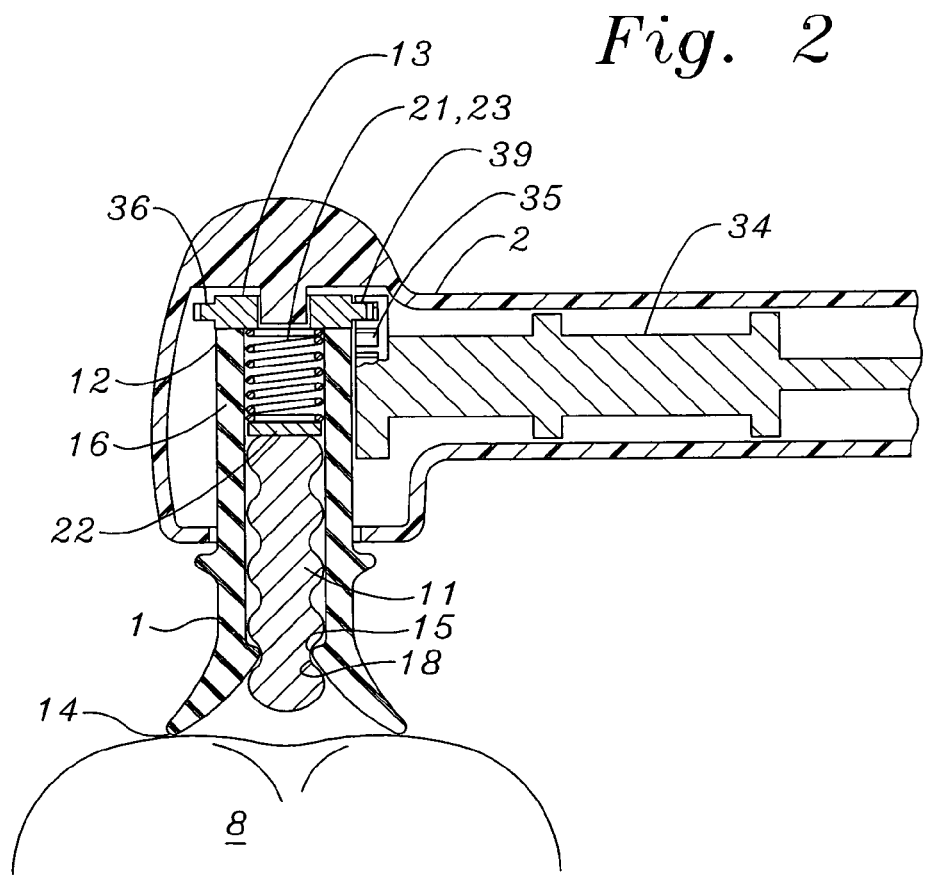
FIG. 2 is a x-sectional view of the prophy cup containing the prophy polish.

Referring to FIG. 1 a prophy cup 1 is shown attached to a prophy angle dental handpiece 2 which is then attached to a dental handpiece 3. The dental handpiece 3 provides rotating power to the prophy angle 2 which in turn rotates the prophy cup 1. The prophy cup is used in combination with a prophy polish in cleaning the teeth. In FIG. 2 a preferred embodiment of the invention is shown comprising a prophy cup 1 containing a solid core prophy polish 11.

The prophy cup 1 of the present invention is shown in FIGS. 1–5. The cup 1 is made of a pliable elastomeric material having a durometer hardness of about 42 to about 70. Preferably the cup 1 is made of a natural rubber or polyisoprene containing a small amount of abrasive. The preferred abrasive in the prophy cup 1 is medium and fine grade pumice. Other abrasives can be used such as hard minerals (Mohs hardness 5 to 9) and softer minerals, such as phosphates (Mohs hardness below 5).

Depicted in FIGS. 1–5 the dental prophy cup 1 is comprised of a cylindrical body 12 with a longitudinal axis having a rear mounting portion 13 and a front polishing portion 14. The rear mounting portion 13 has a recess, or in the alternative, a shaft 17 for attachment to a conventional prophy handpiece 2 for rotation about the long axis of the body 12. The front polishing portion 14 includes a front surface 15 which defines a skirt which slopes outwardly towards the front, the diameter of the bottom skirt being greater than the top of the skirt. The top of the skirt defines an annular retaining edge 15, which retains the solid core prophy polish 12. The body 12 of the prophy cup 1 is defined by a wall 16 with an inside and an outside. The inside wall is smooth and encloses the solid core prophy polish 11 which has the same axial longitudinal direction as the prophy cup body 12 of the prophy cup 1 and is positioned at the front edge of the inside of the body 12 of the prophy cup 1. Located within the inside of the body of the mounting portion 13 is a force means which applies pressure on the solid core polish 11 which dispenses the polish towards the surface of the tooth 8. As the front polish in the front polishing portion 14 of the prophy cup 1 is pressed against the tooth surface 8 the front polishing portion 14 stretches into a larger diameter which also stretches the retaining side 15 into a larger circumferential diameter which releases the retaining side 15 from the corresponding solid core groove 18. The result is the solid core polish 11 is pressed against the tooth surface by the rear force means 21 and the rotation of the prophy cup 1 releases the prophy polish 11 at a uniform rate. When no loads are placed against the tooth the solid core prophy-polish 11 is retained within the prophy cup 1.

Figure 3:
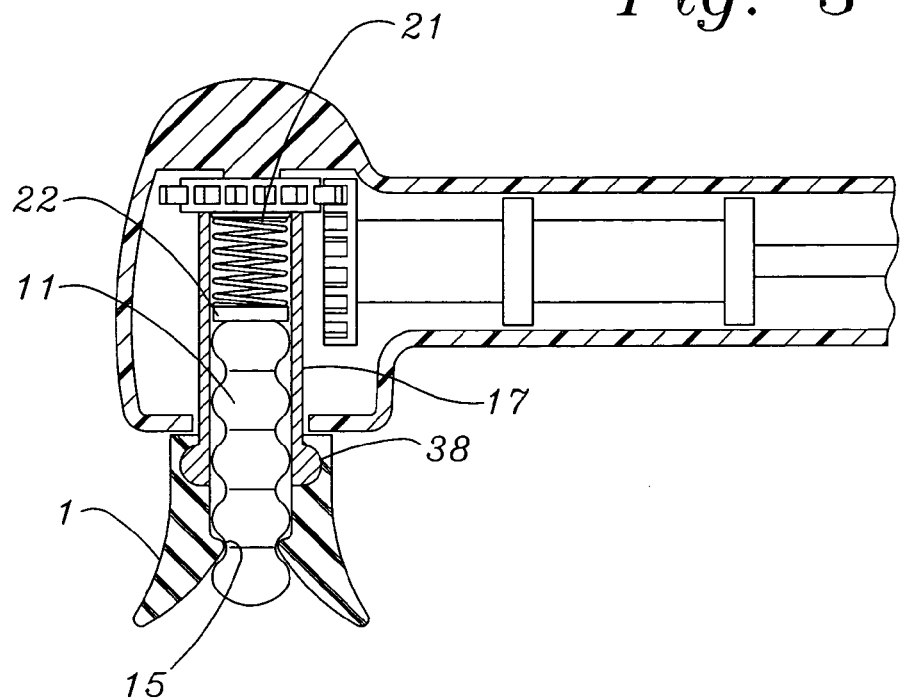
FIG. 3 is a x-sectional view of a preferred embodiment off the all-in-one prophy angle.

In a preferred embodiment in FIGS. 2 and 3 the pressure produced against the solid core prophy polish 11 is produced by an internal spring 21 at the rear end of the prophy cup 1. The spring pressure is applied to a circular piston which in turn transmits the pressure to the solid core prophy polish 11.

In FIG. 3 is another preferred embodiment. The shaft 17 is hollow with a 2–4 mm. internal open diameter. The piston is located adjacent to the rear end. The front end of the shaft 17 is a bulbous ball 38 which the prophy cup 1 is fitted and attached to. The prophy cup 1 and the solid core prophy polish 11 may be replaced.

Figure 4:
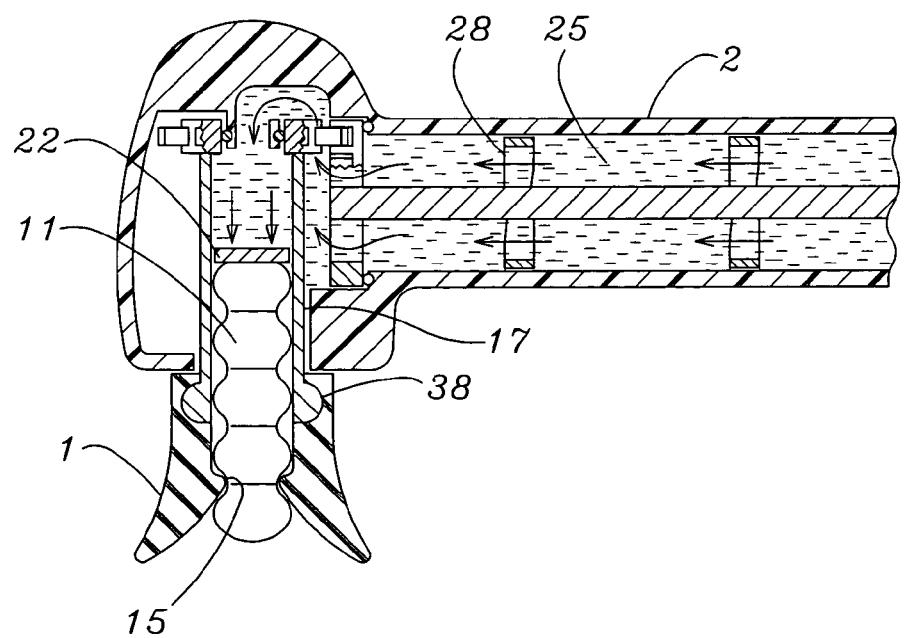
FIG. 4 is a x-sectional view of a preferred embodiment off the all-in-one prophy angle.

In FIG. 4 is another embodiment wherein the means to extrude the solid core prophy polish 11 is liquid or air delivered by a rotational paddle 28 within the prophy angle which delivers the force to the piston which in turn moves the solid core polish 11.

Figure 5:
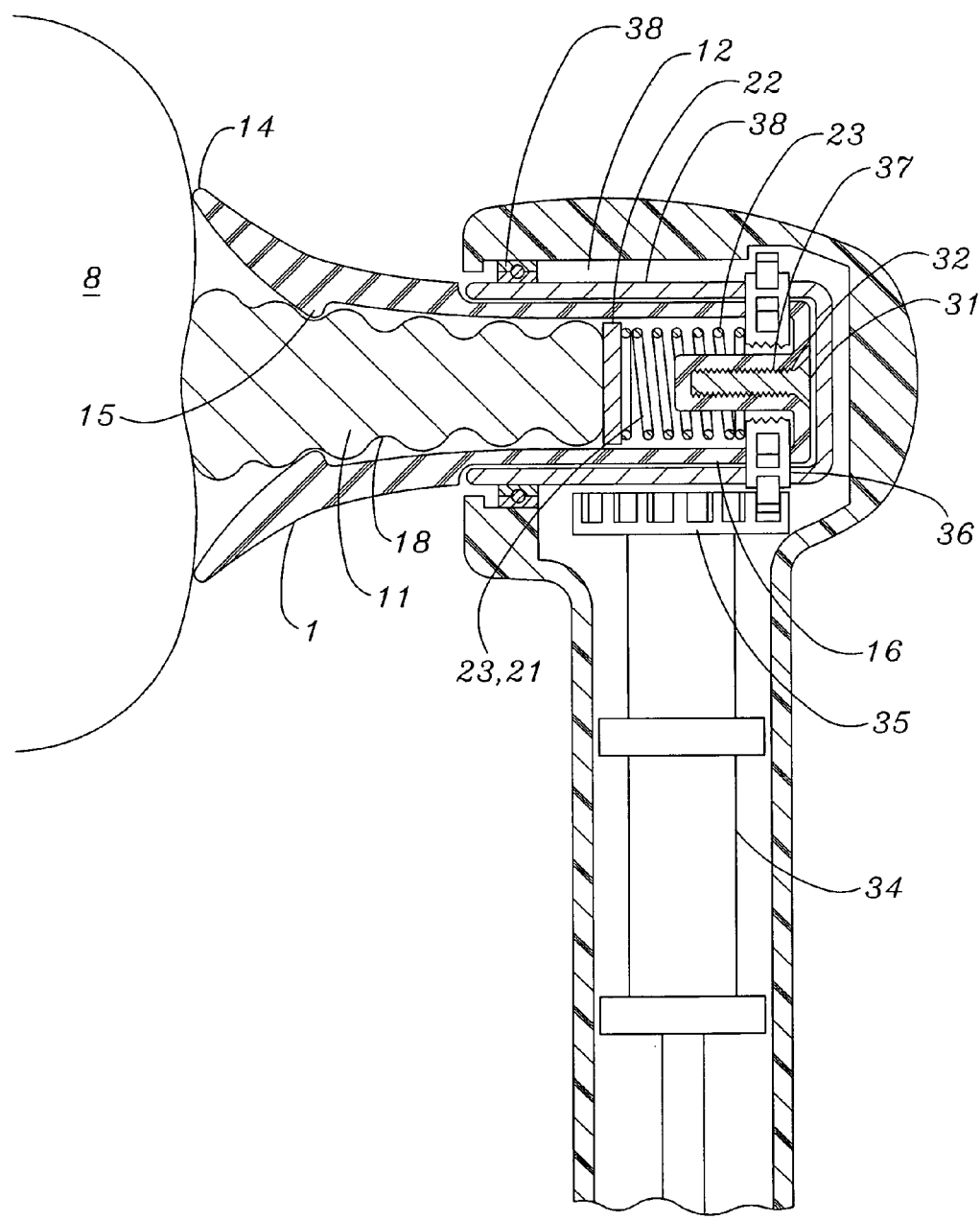
FIG. 5 is a x-sectional view of a preferred embodiment off the all-in-one prophy angle.

In FIG. 5 is another preferred embodiment wherein the prophy handpiece 2 has an internal cavity which contains a prophy cartridge 38 comprised of metal or plastic which internally contains the wall 16 of the prophy cup 1. The wall of the prophy cup 1 fits the internal wall 16 of the prophy cartridge 38. The wall of the prophy cartridge 38 contains an internal screw 31 which fits into a female screw hole 32 of the prophy cup 1. The prophy cup 1 has an internally contained spring 23, which dispenses the solid core prophy polish 11 towards the tooth surface 6. In this embodiment the prophy cartridge 38 is mounted within the prophy angle 2 with bearings 33 and a drive mechanism. The drive mechanism is comprised of an annular gear 36 attached to the outer circumference of the prophy cartridge 38 which engages with the prophy angle 2 drive gear 35. The prophy angle drive gear 35 is contained and attached within the hollow interior cup-shaped fitting 39 which forms the end of the driveshaft 34 adjacent to the trophy cartridge 38. The entire prophy cartridge 38, containing the prophy cup 1 and solid core prophy polish 11 rotates during cleaning teeth. This embodiment allows for the largest amount of solid core prophy polish 11 and the replaceability of the prophy cup 1 containing the solid core prophy polish 11 by unscrewing the prophy cup 1 and screwing a new cup 1 on. This allows for the use of a second prophy cup 1 with polish 11 and also allows for a sterilizable re-usable prophy angle 2.

The solid core prophy polish 11 is comprised of a dental abrasive from a group consisting of pumice, clay, and diatomaceous earth with curing systems such as sodium silicate (3–4 parts) and methyl salicylate (0.24–1.25 parts). The dental abrasive value (RDA), using the Hefferen method, should be above 200.

What is claimed is:

1. An all-in-one prophy angle comprising:
    an angled prophy handpiece with a driveshaft with first and second ends, the first driveshaft end is mounted to an electrical or air driven dental handpiece;
    an elastomeric dental prophy cup with a longitudinal axial direction, a rear end and a front end with a front polishing portion, an inside and an outside wherein the rear end of the prophy cup is attached to the second driveshaft end of the angled prophy handpiece; and
    a solid core prophy paste with a longitudinal axial direction, a front end and a rear end wherein the solid core prophy paste is contained longitudinally within the inside of the prophy cup.

2. An all-in-one prophy angle as in claim 1 wherein the prophy cup front end flares outwardly towards the front end, the front end is used for polishing the teeth.

3. An all-in-one prophy angle as in claim 1 wherein an annular retaining lip defines the inside of the front end of the prophy cup, the lip retains the solid core prophy paste within the inside of the prophy cup.

4. An all-in-one prophy angle as in claim 1 wherein the solid core paste is defined by circumferential parallel rings positioned at a right angle to the prophy paste's longitudinal axis, the grooves are sized to fit the annular retaining lip which, when seated in the annular groove, retains the prophy paste within the prophy cup.

5. An all-in-one prophy angle as in claim 1 wherein the force means is a spring with a front end and a rear end positioned between the inside rear end of the prophy cup and the rear end of the solid core prophy paste, the spring applying force to the solid core which holds the solid core against the tooth surface during use of the prophy angle.

6. An all-in-one-prophy angle as in claim 1 wherein a cylindrical piston is fitted to the inside diameter of the prophy cup and is positioned between the rear end of the solid core prophy paste and the front end of the spring.

7. An all-in-one prophy angle as in claim 1 wherein the elastomeric prophy cup is comprised of natural rubber or polyisoprene, both with a durometer hardness value of about 40 to about 70.

8. An all-in-one prophy angle as in claim 1 wherein the elastomeric prophy cup contains an abrasive such as pumice or minerals which creates a polishing effect on the tooth surface during the use of the prophy cup.

9. An all-in-one prophy angle cup comprising:
    a prophy angle with containing a driveshaft with first and second ends, the first driveshaft end is attached to power source;
    a hollow 2–6 mm diameter second driveshaft end;
    an elastomeric dental prophy cup with a longitudinal axial direction, a rear end and a front end with a front polishing portion, an inside and an outside wherein the rear end of the prophy cup is attached to the second driveshaft end of the angled prophy handpiece;
    a solid core prophy paste with a longitudinal axial direction, a front end and a rear end wherein the solid core prophy paste is contained longitudinally within the inside of the prophy cup the paste extends from the front of the prophy cup into the hollow interior of the prophy drive shaft; and
    a force means which applies pressure to the rear end of the solid core prophy paste.

10. An all-in-one prophy angle as in claim 9 wherein the prophy cup front end defines a skirt which flares outwardly towards the front end, the skirt is used for polishing the teeth.

11. An all-in-one prophy angle as in claim 9 wherein an annular retaining lip defines the inside of the front end of the prophy cup, the lip retains the solid core prophy paste within the inside of the prophy cup.

12. An all-in-one prophy angle as in claim 9 wherein the solid core paste is defined by circumferential parallel rings positioned at a right angle to the prophy paste's longitudinal axis, the grooves are sized to fit the annular retaining lip which, when seated in the annular groove, retains the prophy paste within the prophy cup.

13. An all-in-one prophy angle as in claim 9 wherein the force means is a spring with a front end and a rear end positioned between the inside rear end of the prophy cup and the rear end of the solid core prophy paste, the spring applying force to the solid core which holds the solid core against the tooth surface during use of the prophy angle.

14. An all-in-one-prophy angle as in claim 9 wherein a cylindrical piston is fitted to the inside diameter of the prophy cup and is positioned between the rear end of the solid core prophy paste and the front end of the spring.

15. An all-in-one prophy angle as in claim 9 wherein the elastomeric prophy cup is comprised of natural rubber or polyisoprene, both with a durometer hardness value of about 40 to about 70.

16. An all-in-one prophy angle as in claim 9 wherein the elastomeric prophy cup contains an abrasive such as pumice or minerals which creates a polishing effect on the tooth surface during the use of the prophy cup.

17. An all-in-one prophy angle comprising:
   a prophy angle with an internal containing a driveshaft with first and second ends, the first driveshaft end is attached to power source;
   a hollow 2–6 mm diameter second driveshaft end;
   an elastomeric dental prophy cup with a longitudinal axial direction, a rear end and a front end with a front polishing portion, an inside and an outside wherein the rear end of the prophy cup extends and is contained within the second end driveshaft hollow interior;
   a solid core prophy paste with a longitudinal axial direction, a front end and a rear end wherein the solid core prophy paste is contained longitudinally within the inside of the prophy cup the paste extends from the front of the prophy cup into the hollow interior of the prophy drive shaft; and
   a force means which applies pressure to the rear end of the solid core prophy paste.

18. An all-in-one prophy angle as in claim 17 wherein the prophy cup front end flares outwardly towards the front end, the front end is used for polishing the teeth.

19. An all-in-one prophy angle as in claim 17 wherein an annular retaining lip defines the inside of the front end of the prophy cup, the lip retains the the solid core prophy paste within the inside of the prophy cup.

20. An all-in-one prophy angle as in claim 17 wherein the solid core paste is defined by circumferential parallel rings positioned at a right angle to the prophy paste's longitudinal axis, the grooves are sized to fit the annular retaining lip which, when seated in the annular groove, retains the prophy paste within the prophy cup.

21. An all-in-one prophy angle as in claim 17 wherein the force means is a spring with a front end and a rear end positioned between the inside rear end of the prophy cup and the rear end of the solid core prophy paste, the spring applying force to the solid core which holds the solid core against the tooth surface during use of the prophy angle.

22. An all-in-one-prophy angle as in claim 17 wherein a cylindrical piston is fitted to the inside diameter of the prophy cup and is positioned between the rear end of the solid core prophy paste and the front end of the spring.

23. An all-in-one prophy angle as in claim 17 wherein the elastomeric prophy cup is comprised of natural rubber or polyisoprene, both with a durometer hardness value of about 40 to about 70.

24. An all-in-one prophy angle as in claim 17 wherein the elastomeric prophy cup contains an abrasive such as pumice or minerals which creates a polishing effect on the tooth surface during the use of the prophy cup.

25. An all-in-one prophy angle as in claim 17 wherein the prophy angle is comprised of internal rotational paddles which propel air or a liquid when the prophy angle is run, the air or liquid provides the extruding force means against the solid core prophy paste.

* * * * *